United States Patent
Berney et al.

(10) Patent No.: US 7,019,004 B2
(45) Date of Patent: Mar. 28, 2006

(54) HYDANTOIN DERIVATIVES WITH AFFINITY FOR SOMATOSTATIN RECEPTORS

(75) Inventors: Daniel Berney, Lausanne (CH); Robin Breckenridge, Hagenthal-le-bas (FR); Peter Neumann, Bern (CH); Gideon Shapiro, Gainesville, FL (US); Max Peter Seiler, Riehen (CH); Thomas J. Troxler, Wahlen (CH)

(73) Assignee: Novartis AG, Basel (CH)

( * ) Notice: Subject to any disclaimer, the term of this patent is extended or adjusted under 35 U.S.C. 154(b) by 26 days.

(21) Appl. No.: 10/333,388

(22) PCT Filed: May 7, 2001

(86) PCT No.: PCT/EP01/05162

§ 371 (c)(1),
(2), (4) Date: Aug. 14, 2003

(87) PCT Pub. No.: WO01/85718

PCT Pub. Date: Nov. 15, 2001

(65) Prior Publication Data

US 2004/0110779 A1 Jun. 10, 2004

(30) Foreign Application Priority Data

May 8, 2000 (GB) .................................. 0011071

(51) Int. Cl.
*A61K 31/5377* (2006.01)
*A61K 31/4178* (2006.01)
*C07D 401/14* (2006.01)
*C07D 403/14* (2006.01)
*C07D 413/14* (2006.01)

(52) U.S. Cl. ............... 514/235.2; 514/254.05; 514/323; 514/339; 514/391; 544/139; 544/373; 546/201; 548/305.1; 548/306.1; 548/311.4; 548/312.1

(58) Field of Classification Search ............... 544/373, 544/139; 546/201, 274.4; 548/305.1, 306.1, 548/311.4, 312.1; 514/235.2, 254.05, 323, 514/339, 391
See application file for complete search history.

(56) References Cited

U.S. PATENT DOCUMENTS 5,859,190 A * 1/1999 Meyer et al. ............. 530/331
2003/0191134 A1* 10/2003 Shapiro et al. ......... 514/254.05

FOREIGN PATENT DOCUMENTS

WO     WO 01/09090 A2    2/2001
WO     2003/042234     * 5/2003

OTHER PUBLICATIONS

Yang, Annual Reports in Medicinal Chemistry, vol. 34, p. 209-218 (1999).*
Sciciński et al., "The Solid Phase Synthesis of a Series of Tri-Substituted Hydantoin Ligands for the Somatostatin $SST_5$ Receptor", *Bioorg. Med. Chem. Lett.*, vol. 8, No. 24, pp. 3609-3614 (1998).

* cited by examiner

*Primary Examiner*—Emily Bernhardt
(74) *Attorney, Agent, or Firm*—Peter J. Waibel; E. Jay Wilusz

(57) ABSTRACT

The invention provides compounds of formula (I) wherein X, Y, $R_1$, $R_2$, $R_3$ and $R_4$ are as defined in the description, and the preparation thereof. The compounds of the formula bind to somatostatin receptors and are useful as pharmaceuticals

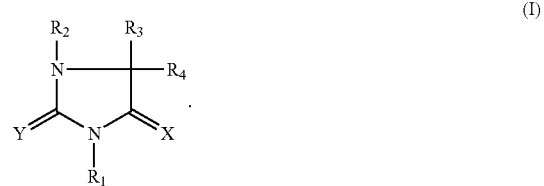

4 Claims, No Drawings

HYDANTOIN DERIVATIVES WITH AFFINITY FOR SOMATOSTATIN RECEPTORS

The present invention relates to novel hydantoin derivatives, their preparation, their use as pharmaceuticals and pharmaceutical compositions containing them.

The invention provides compounds of formula I

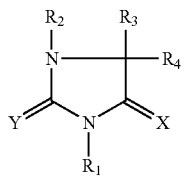

wherein
X and Y independently are O or H, H,
$R_1$ is a group of formula

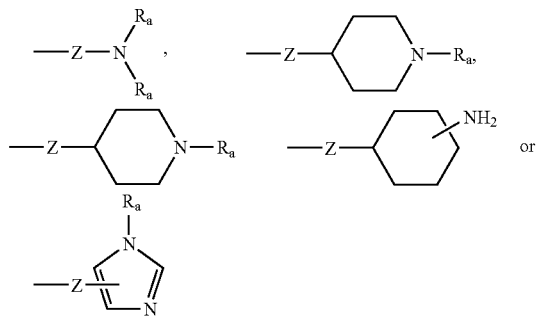

wherein the $R_a$ independently are hydrogen, $C_{1-4}$ alkyl or a $CH_3COO—CH(CH_3)—OCO—$ group and Z is a saturated or unsaturated aliphatic $C_{2-6}$ hydrocarbonic chain which is (a) optionally interrupted by —O— or —S— and (b) optionally substituted by $C_{1-4}$ alkyl or $C_{1-4}$ alkoxy groups, $R_2$ is a group of formula —$SO_2$—Ar or —$CH_2$—Ar wherein Ar is phenyl or naphthyl optionally mono- or di-substituted by hydroxy, halogen, $C_{1-4}$ alkyl, $C_{1-4}$ alkoxy, cyano, trifluoromethyl, aminomethyl, dimethylaminocarbonyl, benzimidazolyloxy or morpholinocarbonyl, or by a group of formula

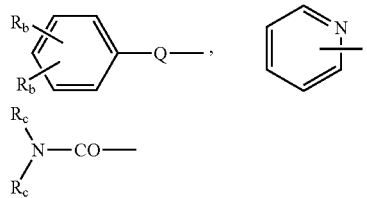

wherein Q is $CH_2$, O, S or CO, the $R_b$ independently are hydrogen, $C_{1-4}$alkyl, $C_{1-4}$alkoxy, amino, halogen, hydroxy, a $NH_2—(CH_2)_4—CH(NH_2)—COO—$ group or form together a methylenedioxy, and the $R_c$ independently are hydrogen or $C_{1-4}$alkyl, $R_3$ is hydrogen or $C_{1-4}$ alkyl and
$R_4$ is a group of formula

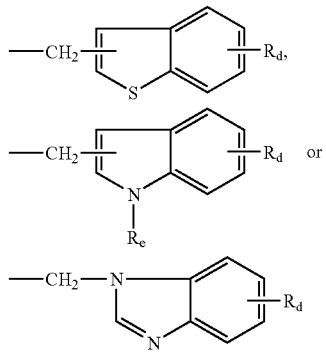

wherein $R_d$ is hydrogen, halogen, $C_{1-4}$ alkyl or $C_{1-4}$alkoxy, and $R_e$ is hydrogen, $C_{1-4}$alkyl or benzyl, in free base or acid addition salt form.
X and Y are preferably O.
$R_1$ preferably is —Z—$NH_2$, wherein Z is preferably an alkylene chain.
$R_2$ preferably is —$SO_2$—$A_r$, wherein $A_r$ is preferably an optionally substituted phenyl.
$R_3$ preferably is H.
$R_4$ is preferably an optionally substituted 3-indolyl.
Any alkyl or alkoxy group as defined above preferably has one or two carbon atoms and more preferably is methyl or methoxy.
Halogen denotes fluorine, bromine or chlorine.

Depending on the nature of the substituents defined above, one or more asymmetric carbons may be present in the molecule. All optical isomers and their mixtures including the racemic mixtures are part of the present invention.

The compounds of formula I may be prepared over a process which includes the steps of reacting a compound of formula II

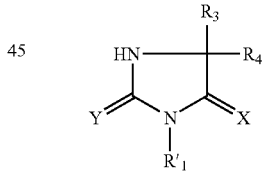

wherein X, Y, $R_3$ and $R_4$ are as defined above and $R'_1$ is $R_1$ as defined above or a protected form of $R_1$, with a compound of formula III R'$_2$-Hal     III wherein $R'_2$ is $R_2$ as defined above or a protected form of $R_2$ and Hal is chlorine, bromine or iodine, deprotecting the resulting product and recovering the thus obtained compound of formula I in free base or acid addition salt form.

A protected amino group in $R'_1$ is for example an N-butyloxycarbonyl (Boc)- or an $N_3$-residue. When in formula III, $R'_2$ is a group of formula —$SO_2$—$A_r$, Hal is preferably chlorine. The condensation of the compound of formula II with the compound of formula III and the subsequent deprotection can be effected according to known methods, for example as described in Example 1.

Working up the reaction mixtures obtained and purification of the compounds of formula I may also be carried out in accordance with known methods.

Acid addition salts may be produced from the free bases in known manner, and vice versa.

The starting compounds of formula II are known or may be produced by known methods. For example compounds of formula II wherein X and Y are O may be produced in accordance with the following reaction scheme, for example as described in Example 1:

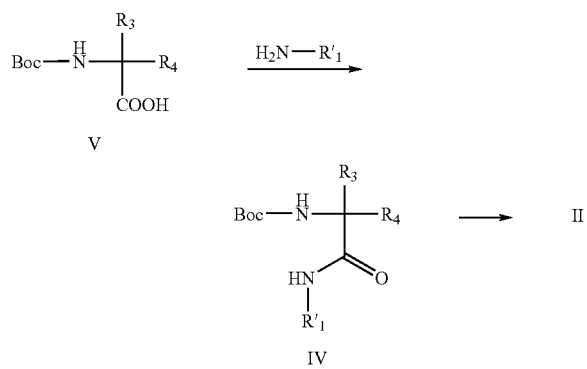

The starting compounds of formulae III and V are known or may be produced by known processes.

The compounds of formula I and their physiologically acceptable acid addition salts, hereinafter referred to as compounds of the invention, have interesting pharmacological properties when tested in vitro using somatostatin receptor expressing cell cultures and in animals, and may therefore be used as pharmaceuticals.

In particular the compounds of the invention bind to somatostatin receptors. More particularly they are selective agonists at Somatostatin $sst_2$ receptors, as determined in radioligand binding and second messenger studies [see for example K. Kaupmann et al., FEBS LETTERS 1993, 331: 53–59].

The compounds of the invention are therefore indicated for use in anxiety, depression, schizophrenia, neurodegenerative diseases such as dementia, epilepsy, endocrinological disorders associated with an excess of hormone release such as: growth hormone (GH) glucagon or insulin secretion, gastro-intestinal disorders, for the treatment of tumors and for vascular disorders and immunological diseases.

The usefulness of the compounds of the invention in these indications is confirmed in a range of standard tests as indicated below:

At doses of about 0.3 to 3 mg/kg p.o., the compounds of the invention increase exploratory behavior of mice in the open half of the half enclosed platform, a model which is predictable for anxiolytic activity (Psychopharmacology, 1986, 89:31–37).

In the same half enclosed platform model, the compounds of the invention at the above indicated doses increase vigilance and exploratory components of behavior of the mice. The compounds are therefore indicated for the treatment of depression, schizophrenia and dementia, in particular of senile dementia of the Alzheimer type (SDAT). In addition, there is circumstantial clinical evidence for various types of dementias to be associated with reduced somatostatin levels [see for example J. Epelbaum et al., Clinical Reviews in Neurobiology 8: 25–44 (1994)].

At doses of about 0.3 to 3 mg/kg p.o., the compounds of the invention inhibit epileptic seizure in electrically and chemically induced episodes in rats [A. Vezzani et al., Neuropharmacol., 30: 345–352 (1991)].

Furthermore the compounds of the invention inhibit GH release in cultured pituitary cells in vitro and depress serum GH and insulin levels in the rat The test is carried out using male rats. The test substance is administered at varying, logarithmically staggered doses employing at least 5 rats per dose. 1 hour after s.c. administration of the test substance blood is taken. The determination of the blood serum GH and insulin levels is measured by radio-immunoassay. The compounds of the invention are active in this test when administered at a dosage in the range of from 0.1 to 1 mg/kg s.c.

The inhibitory effect of the compounds on GH release may also be examined after oral application to male rats with oestradiol implants. This test is carried out as follows:

A loop (length 50 mm Ø 3 mm) of silastic with 50 mg of oestradiol is implanted under the dorsal skin of anaesthetized male OFA rats which have a weight of ca. 300 g. At various times (1 to 6 months later), these animals, in a fasted state, are used repeatedly for tests. The test substances are active in this test at doses from 0.1 to 5 mg/kg, when GH level in the blood serum is determined by radio-immunoassay 1 and 2 hours after oral administration.

The compounds of the invention are accordingly indicated for use in the treatment of disorders with an aetiology comprising or associated with excess GH-secretion, e.g. in the treatment of acromegaly as well as in the treatment of diabetes mellitus, especially complications thereof, e.g. angiopathy and various disorders associated with angiogenesis, proliferative retinopathy, dawn phenomenon and nephropathy.

The compounds of the invention also inhibit gastric and exocrine and endocrine pancreatic secretion and the release of various peptides of the gastrointestinal tract, as indicated in standard tests using e.g. rats with gastric or pancreatic fistulae.

The compounds are thus additionally indicated for use in the treatment of gastro-intestinal disorders, for example in the treatment of peptic ulcers, disturbances of GI motility, enterocutaneous and pancreaticocutaneous fistula, irritable bowel syndrome, dumping syndrome, watery diarrhea syndrome, acute pancreatitis and gastro-intestinal hormone secreting tumors (e.g. vipomas, glucagonomas, insulinomas, carcinoids and the like) as well as gastro-intestinal bleeding. [see for example: Th. O'Dorisio et al., Advances Endocrinol. Metab. 1990,1:175–230].

The compounds of the invention are also effective in the treatment of various kinds of tumors, particularly of $sst_2$ receptor bearing tumors, as indicated in proliferation tests with various different cancer cell lines and in tumor growth experiments in nude mice with hormone dependent tumors [see for example: G. Weckbecker et al., Cancer Research 1994, 54: 6334–6337]. Thus the compounds can be used in the treatment of, for example, cancers of the breast, the prostate, the colon, the pancreas, the brain and the lung (small cell lung cancer).

For the above-mentioned indications, the appropriate dosage will of course vary depending upon, for example, the compound employed, the host, the mode of administration and the nature and severity of the condition being treated. However, in general, satisfactory results in animals are indicated to be obtained at a daily dosage of from 0.1 to about 50, preferably from about 0.5 to about 20 mg/kg animal body weight. In larger mammals, for example humans, an indicated daily dosage is in the range from about 1 to about 100, preferably from about 5 to about 50 mg of an agent of the invention conveniently administered, for example, in divided doses up to four times a day or in sustained release form.

The compounds of the invention may be administered in free form or in pharmaceutically acceptable salt form or complexes. Such salts and complexes may be prepared in conventional manner and exhibit the same order of activity as the free compounds.

The present invention also provides a pharmaceutical composition comprising a compound of the invention in free base form or in pharmaceutically acceptable acid addition salt form in association with a pharmaceutically acceptable diluent or carrier. Such compositions may be formulated in conventional manner. The compounds may be administered by any conventional route, for example parenterally e.g. in form of injectable solutions or suspensions, enterally, preferably orally, e.g. in the form of tablets or capsules or in a nasal or a suppository form.

Moreover the present invention provides the use of the compounds of the invention for the manufacture of a medicament for the treatment of any condition mentioned above.

In still a further aspect the invention provides a method for the treatment of any condition mentioned above, in a subject in need of such treatment, which comprises administering to such subject a therapeutically effective amount of a compound of the invention.

The following examples illustrate the invention. The temperatures are given in degrees Celsius and are uncorrected.

EXAMPLE 1

(+/−)-1-(2',5'-dichloro-1'-benzenesulfonyl)-3-(5'-amino-n-pentanyl)-5-[(indol-3-yl)-methyl)]-imidazolidine-2,4-dione Sodium hexamethyldisilazide (1.1 mmol, 1.1 mL 1 M solution in THF) is added to a stirred solution of 3-[5'-amino-(N-t-butyloxycarbonyl)-n-pentanyl]-5-[(indol-3-yl)methyl]-imidazolidine-2,4-dione (415 mg, 1.0 mmol) in 5 mL dry tetrahydrofuran (THF) at −40° under argon. After 30 minutes, 2,5-dichlorobenzenesulfonyl chloride (270 mg, 1.1 mmol) is added and the solution is allowed to stir overnight at room temperature. Saturated ammonium chloride solution is added and the mixture concentrated on a rotary evaporator. The mixture is then dissolved in ethyl acetate, extracted with brine, dried (sodium sulfate) and concentrated to a viscous oil. This crude product is purified by medium pressure liquid chromatography (MPLC) over silica gel (59 g $SiO_2$ 0.015–0.04 mm; ethylacetate-hexane 2:1) to give a colorless viscous oil.

The so obtained product (530 mg, 0.85 mmol) is dissolved in 6 mL of dichloromethane and iodotrimethylsilane (204 mg, 2.0 mmol) is added. After stirring for 10 minutes at room temperature, potassium bicarbonate (4 mL, 2N solution) is added and the resulting solution stirred for 15 minutes. The organic phase is separated, dried (sodium sulfate) and concentrated to give the crude free base. This base is dissolved in 4 mL ethanol and ethereal HCl solution (1 mL, ca. 1N solution) is added. The solution is cooled and ether added whereupon the hydrochloride salt crystallizes out of solution. Filtration provides the product in hydrochloride salt form; mp. 157–159°.

The starting imidazolidine-dione is prepared as follows:

a) N-α-t-butyloxycarbonyl-d,l-tryptophan-[5-amino-(N-t-butyloxycarbonyl)-n-pentanyl] amide To a stirred solution of mono-N-Boc-1,5-pentanediamine (1.27 g, 6.3 mmol) and d,l-tryptophan (2.12 g, 7.0 mmol) in 30 mL THF is added dicyclohexylcarbodiimide (DCC) (1.54 g, 7.5 mmol) at room temperature. After one hour the mixture is filtered to remove the precipitated dicydohexylurea and concentrated in vacuo. Ether is added, the mixture is filtered and then cooled, whereupon the product crystallizes out of solution. Filtration yields the product as a light brown powder; mp. 97–98°.

b) 3-[5'-amino-(N-t-butyloxycarbonyl)-n-pentanyl]-5-[(indol-3-yl)methyl)]-imidazolidine 2,4-dione The product obtained under a) (2.93 g, 6.0 mmol) is dissolved in 50 mL THF and heated under reflux with tetrabutylammonium fluoride trihydrate (5.68 g, 18 mmol). After 24 hours the mixture is concentrated in vacuo. The residue is dissolved in ethylacetate, extracted with brine, dried (sodium sulfate) and concentrated to a viscous brown oil. MPLC chromatography (138 g $SiO_2$; ethylacetate-hexane 2:1) gives the product as a light yellow oil which crystallizes upon standing. An analytical sample is prepared by recrystallization from ethylacetate-hexane; mp. 136–137°.

The compounds of formula I wherein $R_1$, $R_2$, $R_3$ and $R_4$ are as defined in the following table 1 and X and Y are both O as well as the compounds of formula I wherein $R_1$, $R_2$, $R_3$ and $R_4$ are as defined in the following table 2, X is H, H and Y is O, are prepared in analogous manner to Example 1.

TABLE 1

| Ex | $R_1$ | $R_2$ | $R_3$ | $R_4$ |
|----|-------|-------|-------|-------|
| 2 | —(CH$_2$)$_5$—NH$_2$ | —SO$_2$-p-toluyl | H | —CH$_2$-3 indolyl |
| 3 | " | —SO$_2$-3,4-diMe—Ph | " | " |
| 4 | " | —SO$_2$-m-CH$_3$—Ph | " | " |
| 5 | " | —SO$_2$-o-OMe—PH | " | " |
| 6 | —CH$_2$CH═CH—(CH$_2$)$_2$—NH$_2$ (cis) | —SO$_2$-3,4-diOMe—Ph | " | " |
| 7 | —(CH$_2$)$_2$—O—(CH$_2$)$_2$—NH$_2$ | —SO$_2$-3,4-diOMe—Ph | " | " |
| 8 | —(CH$_2$)$_4$—NH$_2$ | —SO$_2$-3,4-diOMe—Ph | " | " |
| 9 | —(CH$_2$)$_6$—NH$_2$ | —SO$_2$-3,4-diOMe—Ph | " | " |
| 10 | —(CH$_2$)$_5$—NH$_2$ | —SO$_2$-3-[(Me)$_2$NCO]-4-(5-benzimidazolyl-O)—Ph | " | " |
| 11 | " | —SO$_2$-p-(p-NH$_2$—Ph—O)—Ph | " | " |
| 12 | " | —SO$_2$-3-CN-4-(p-OH—Ph—O)—Ph | " | —CH$_2$-3-(7-CH$_3$-indolyl) |
| 13 | " | —SO$_2$-3-NH$_2$CH$_2$-4-(p-OH—Ph—O)—ph | " | —CH$_2$-3-(7-CH$_3$-indolyl) |
| 14 | " | —SO$_2$-p-(p-OH—Ph—CO)—Ph | " | —CH$_2$-3-indolyl |

TABLE 1-continued

| Ex | $R_1$ | $R_2$ | $R_3$ | $R_4$ |
|---|---|---|---|---|
| 15 | " | —SO$_2$-p-(p-OH—Ph—CH$_2$)—Ph | " | " |
| 16 | " | —SO$_2$-p-(p-OH—Ph—O)—Ph | " | " |
| 17 | " | —SO$_2$-p-(—OH—Ph—S)—Ph | " | " |
| 18 | " | —SO$_2$-p-(4-NH$_2$-2-pyridyl-O)—Ph | " | " |
| 19 | " | —SO$_2$-3-(morpholino-CO)-4-(p-Cl—Ph—O)—Ph | H | —CH$_2$-3-indolyl |
| 20 | 4-piperidinyl-(CH$_2$)$_2$— | —SO$_2$-3-[(Me)$_2$NCO]-4-(p-OH—Ph—O)—Ph | " | " |
| 21 | —(CH$_2$)$_5$—NH$_2$ | —SO$_2$-3-[(Me)$_2$NCO]-4-(3-Cl-4-OH—Ph—O)—Ph | " | " |
| 22 | 4-Me-1-piperazinyl-(CH$_2$)$_2$— | —SO$_2$-3-[(Me)$_2$NCO]-4-(p-OMe—Ph—O)—Ph | " | " |
| 23 | —(CH$_2$)$_5$—NH$_2$ | —SO$_2$-3-[(Me)$_2$NCO]-4-[NH$_2$—(CH$_2$)$_4$—CH(NH$_2$)—COO—Ph—O]—Ph | " | " |
| 24 | [MeCOO—CH(Me)—OCO—NH]—(CH$_2$)$_5$— | —SO$_2$-3-[(Me)$_2$NCO]-4-(p-OH—Ph—O)—Ph | " | " |
| 25 | —(CH$_2$)$_5$—NH$_2$ | —SO$_2$-3-[(Me)$_2$NCO]-4-(3-Cl-4-OH—Ph—O)—Ph | " | —CH$_2$-3-(7-Cl-indolyl) |
| 26 | —CH$_2$-(p-trans-NH$_2$-cyclohexyl) | —SO$_2$-3-[(Me)$_2$NCO]-4-(p-OH—Ph—O)—Ph | " | —CH$_2$-3-indolyl |
| 27 | —(CH$_2$)$_5$—N(Me)$_2$ | —SO$_2$-3-[(Me)$_2$NCO]-4-(3-Cl-4-OH—Ph—O)—Ph | " | " |
| 28 | —(CH$_2$)$_3$-(1-imidazolyl) | —SO$_2$-3-[(Me)$_2$NCO]-4-(3-Cl-4-OH—Ph—O)—Ph | " | " |
| 29 | —(CH$_2$)$_5$—NH$_2$ | —SO$_2$-3-[(Me)$_2$NCO]-4-(3-Cl-4-OH—Ph—O)—Ph | " | —CH$_2$-3-(7-Me-indolyl) |
| 30 | —(CH$_2$)$_5$—NH$_2$ | —SO$_2$-3-[(Me)$_2$NCO]-4-(3-Cl-4-OH—Ph—O)—Ph | H | —CH$_2$-3-(5-Me-indolyl) |
| 31 | —(CH$_2$)$_4$—CH(Me)$_2$—NH$_2$ | —SO$_2$-3-[(Me)$_2$NCO]-4-(3-Cl-4-OH—Ph—O)—Ph | " | —CH$_2$-3-(7-Me-indolyl) |
| 32 | —(CH$_2$)$_3$-(1-Me-4-imidazolyl) | —SO$_2$-3-[(Me)$_2$NCO]-4-(3-Cl-4-OH—Ph—O)—Ph | " | —CH$_2$-3-indolyl |
| 33 | —(CH$_2$)$_5$—NH$_2$ | —SO$_2$-3-CH(CH$_3$)$_2$-4-(3-Cl-4-OH—Ph—O)—Ph | " | —CH$_2$-3-(7-Me-indolyl) |
| 34 | —(CH$_2$)$_4$—C(CH$_3$)$_2$—NH$_2$ | —SO$_2$-3-[(Me)$_2$NCO]-4-(p-F—Ph—O)—Ph | " | " |
| 35 | " | —CH$_2$-3-[(Me)$_2$NCO]-4-(3-Cl-4-MeO—Ph—O)—Ph | " | " |
| 36 | " | —SO$_2$-3-[(Me)$_2$NCO]-4(3,4-diCl—Ph—O)—Ph | " | " |
| 37 | " | —SO$_2$-3-[(Me)$_2$NCO]-4-(3-Cl-4-OH—Ph—O)—Ph | " | —CH$_2$-3-benzo[b]thienyl |
| 38 | " | —SO$_2$-3-[(Me)$_2$NCO]-4-(3-Cl-4-MeO—Ph—O)—Ph | " | —CH$_2$-1-(4-Me-benzimidazolyl) |
| 39 | —(CH$_2$)$_4$—C(CH$_3$)$_2$—NH$_2$ | —SO$_2$-3-[(Me)$_2$NCO]-4-[(3,4-methylenedioxy-Ph—O)]—Ph | " | —CH$_2$-3-(7-Me-indolyl) |

Me = methyl;
Ph = phenyl

TABLE 2

| Ex | $R_1$ | $R_2$ | $R_3$ | $R_4$ |
|---|---|---|---|---|
| 40 | —CH$_2$—CH=CH—(CH$_2$)$_2$—NH$_2$ | —CH$_2$—Ph | H | —CH$_2$-3-indolinyl |
| 41 | " | " | " | —CH$_2$-3-indolyl |
| 42 | —(CH$_2$)$_5$—NH$_2$ | " | " | " |
| 43 | —CH$_2$-p-(aminomethyl)-Ph | " | " | " |
| 44 | —(CH$_2$)$_5$—NH$_2$ | —SO$_2$-3,4-dioMe—Ph | " | " |
| 45 | " | —SO$_2$-p-(p-OH—Ph—O)—Ph | " | " |

Me = methyl;
Ph = phenyl

The compounds of the above tables have been characterized as follows:

| Example | | | |
|---|---|---|---|
| 2 | FAB-MS: | MH$^+$ = 469 | |
| 2 | FAB-MS: | MH$^+$ = 515 | |
| 4 | FAB-MS: | MH$^+$ = 523 | |

-continued

|  |  |  |
|---|---|---|
| 8 | FAB-MS: | MH⁺ = 515 |
| 9 | FAB-MS: | MH⁺ = 529 |
| 12 | FAB-MS: | MH⁺ = 602 |
|  | NMR(DMSO): | 0.4–1.1(6H, m), 2.3(2H, t), 2.4(3H, s), 2.9(1H, m), 3.05 (1H, m), 3.2–2.6(2H, s), 3.5(2H, d), 5.2(1H, t), 6.8–7.1 (9H, m), 7.3(1H, m), 8.2(1H, m), 8.55(1Hm), 11.0(1H, s). |
| 13 | FAB-MS: | MH⁺ = 606 |
|  | NMR(DMSO): | 0.4–1.6(6H, m), 2.4(3H, t), 2.5(2H, m), 2.9(1H, m), 3.1 (1H, m), 3.5(2H, m), 4.2(2H, m), 5.25(1H, m), 6.7–7.1 (8H, m), 7.35(1H, m), 7.9(1H, m), 8.05(3H, s), 8.3(1H, m), 8.75(3H, s), 9.75(1H, s), 11.1(1H, s). |
| 14 | Mp: | 151–153° (HCl salt) |
|  | FAB-MS: | MH⁺ = 575 |
|  | NMR(DMSO): | 0.45–1.1(6H, m), 2.25(2H, m), 2.9(1H, m), 3.05(1H, m), 3.2(2H, s), 3.65(1H, m), 3.7(1H, q), 3.85(3H, s), 5.2(1H, t), 6.9–8.2(13H, m), 11.0(1H, s). |
| 15 | FAB-MS: | MH⁺ = 561 |
|  | NMR(DMSO): | 0.4–1.0(6H, m), 2.25(2H, m), 2.85(1H, m), 3.05(1H, m). 3.2(2H, s), 3.5(2H, d), 3.7(3H, s), 4.0(2H, s), 5.1(1H, t), 6.8–8.0(13H, m), 11.0(1H, s). |
| 16 | FAB-MS: | MH⁺ = 563 |
| 17 | FAB-MS: | MH⁺ = 579 |
| 19 | FAB-MS: | MH⁺ = 694 |
| 20 | FAB-MS: | MH⁺ = 660 |
| 21 | FAB-MS: | MH⁺ = 668 |
|  | NMR(Hcl salt; DMSO): | 0.35–1.2(6H, m), 2.45(2H, m), 2.85(3H, s), 3.0(3H, s), 2.85–3.15(2H, m), 3.5(2H, d), 5.65(1H, t), 6.9–7.1(6H, r 7.2(1H, d), 7.35(1H, d), 7.5(1H, d), 7.75(3H, s), 8.0(2H, rr 10.4(1H, s), 11.1(1H, s). |
| 22 | ESI-MS: | M⁺ = 689 |
| 23 | Mp: | 189–191° (amorphous) |
| 24 | Mp: | 107–111° (amorphous) |
| 25 | Mp: | 198–203° |
| 26 | Mp: | 190–196° (amorphous) |
| 27 | ESI-MS: | M⁺ = 696 |
| 28 | ESI-MS: | M⁺ = 691 |
| 29 | FAB-MS: | MH⁺ = 682 |
| 30 | FAB-MS: | MH⁺ = 682 |
| 31 | FAB-MS: | MH⁺ = 710 |
|  | NMR(DMSO): | 0.45–1.1(6H, m), 0.9(6H, 2s), 2.4(3H, s), 2.85(3H, s), 3.0(3H, s), 2.8–3.1(2H, m), 3.5(2H, d), 5.65(1H, t), 6.8–7.05(6H, m), 7.2(1H, d), 7.3(1H, d), 8.0(2H, m), 11.0(1H, s). |
| 32 | ESI-MS: | M⁺ = 705 |
|  | NMR(DMSO): | 1.1(2H, m), 1.8(2H, t), 2.8(3H, s), 2.95(3H, s), 3.05(2H, m), 3.5(2H, d), 3.55(3H, s), 5.6(1H, t), 6.45(1H, s), 6.85–7.05(5H, m), 7.2–7.5(4H, m), 8.0(2H, m), 10.3(1H, s), 10.95(1H, s) |
| 33 | ESI-MS: | M⁺ = 653 |
| 34 | ESI-MS: | M⁺ = 678 |
| 35 | FAB-MS: | MH⁺ = 674 |
|  | NMR(DMSO): | 0.9(6H, s), 0.8–1.4(6H, m), 2.4(3H, s), 2.8(3H, s), 2.95(3H, s), 3.0–3.5(4H, m), 3.85(3H, s), 4.2(1H, t), 4.35(1H, d), 4.8(1H, d), 6.8–7.35(10H, m), 10.9(1Hs). |
| 36 | FAB-MS: | MH⁺ = 728 |
| 37 | FAB-MS: | MH⁺ = 685 |
| 38 | FAB-MS: | MH⁺ = 697 |
| 39 | ESI-MS: | M⁺ = 704 |

What we claim is:

1. A compounds of formula I

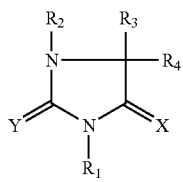

wherein

X and Y independently are O or H, H, $R_1$ is a group of formula

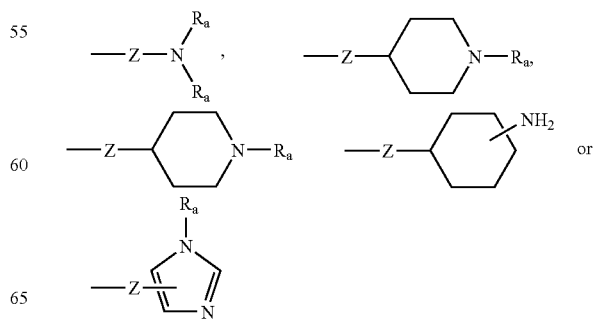

wherein the $R_a$ independently are hydrogen, $C_{1-4}$ alkyl or a $CH_3COO-CH(CH_3)OCO$-group and Z is a saturated or unsaturated aliphatic $C_{2-6}$ hydrocarbonic chain which is (a) optionally interrupted by —O— or —S— and (b) optionally substituted by $C_{1-4}$ alkyl or $C_{1-4}$ alkoxy groups, $R_2$ is a group of formula —$SO_2$—Ar or —$CH_2$—Ar wherein Ar is phenyl or naphthyl optionally mono- or di- substituted by hydroxy, halogen, $C_{1-4}$ alkyl, $C_{1-4}$ alkoxy, cyano, trifluoromethyl, aminomethyl, dimethylaminocarbonyl, benzimidazolyloxy or morpholinocarbonyl, or by a group of formula

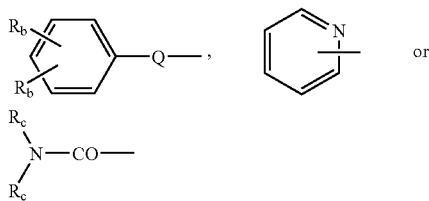

wherein Q is $CH_2$, O, S or CO, the $R_b$ independently are hydrogen, $C_{1-4}$alkyl, $C_{1-4}$alkoxy, amino, halogen, hydroxy, a $NH_2$—$(CH_2)_4$—$CH(NH_2)$—COO— group or form together a methylenedioxy, and the $R_c$ independently are hydrogen or $C_{1-4}$ alkyl, $R_3$ is hydrogen or $C_{1-4}$ alkyl and $R_4$ is a group of formula

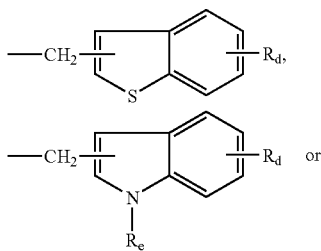

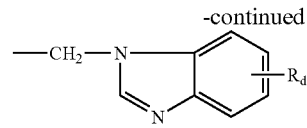

wherein $R_d$ is hydrogen, halogen, $C_{1-4}$ alkyl or $C_{1-4}$alkoxy, and $R_e$ is hydrogen, $C_{1-4}$alkyl or benzyl, in free base or acid addition salt form.

2. A process for the preparation of a compound of formula I as defined in claim 1, which includes the steps of reacting a compound of formula II

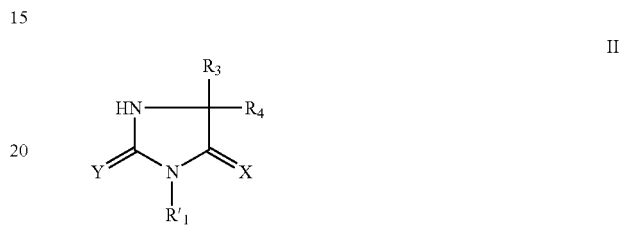

wherein X, Y, $R_3$ and $R_4$ are as defined in claim 1 and $R'_1$ is $R_1$ as defined in claim 1 or a protected form of $R_1$, with a compound of formula III $R'_2$-Hal   III wherein $R'_2$ is $R_2$ as defined in claim 1 or a protected form of $R_2$ and Hal is chlorine, bromine or iodine, deprotecting the resulting product and recovering the thus obtained compound of formula I in free base or acid addition salt form.

3. A pharmaceutical composition comprising a compound of formula I as defined in claim 1 in free base form or in pharmaceutically acceptable acid addition salt form in association with a pharmaceutically acceptable carrier or diluent.

4. A method for treating a subject having a condition selected from the group consisting of anxiety, depression, epilepsy, diabetes mellitus, and acromegaly, which comprises administering to such subject a therapeutically effective amount of a compound of claim 1 in free base or pharmaceutically acceptable acid addition salt form.

* * * * *